United States Patent [19]

Barnett

[11] Patent Number: 5,084,037

[45] Date of Patent: Jan. 28, 1992

[54] MALE EXTERNAL CATHETER URINE COLLECTION SYSTEM AND SHEATH THEREFOR

[76] Inventor: Robert Barnett, 401 SE. Delaware, Unit 108, Ankeny, Iowa 50021

[21] Appl. No.: 562,232

[22] Filed: Aug. 3, 1990

[51] Int. Cl.⁵ .............................................. A61F 5/44
[52] U.S. Cl. ................................. 604/349; 604/350
[58] Field of Search ................ 138/172; 604/346, 347, 604/349, 350, 327; 623/1; 128/760, 767

[56] References Cited

U.S. PATENT DOCUMENTS

| | | | |
|---|---|---|---|
| 1,472,518 | 10/1923 | Gillette et al. | 138/172 |
| 3,091,261 | 5/1963 | Waddell, Jr. | 138/131 |
| 3,141,480 | 7/1964 | Ralston | 138/172 |
| 4,073,295 | 2/1978 | Laufbahn | 604/353 |
| 4,118,262 | 10/1978 | Abbott | 138/172 |
| 4,713,067 | 12/1987 | Rothenberg et al. | 604/353 |
| 4,966,166 | 10/1990 | Leffler | 128/844 |

Primary Examiner—David J. Isabella
Assistant Examiner—R. Clarke
Attorney, Agent, or Firm—Kent A. Herink; Brian J. Laurenzo; Rudolph L. Lowell

[57] ABSTRACT

A male external catheter urine collection system and sheath therefor. The sheath is suspended from a belt worn by a user and receives the user's penis through an open upper end portion thereof that has an inwardly rolled-over peripheral edge. Urine in the sheath is discharged to an outlet tube through a discharge opening in a tapered lower end portion of the sheath. A coil spring associated with the outlet tube prevents the outlet tube from kinking shut during use. A discharge tube connects to the outlet tube and carries the discharged urine to a collection bag strapped to the lower leg of the user.

10 Claims, 2 Drawing Sheets

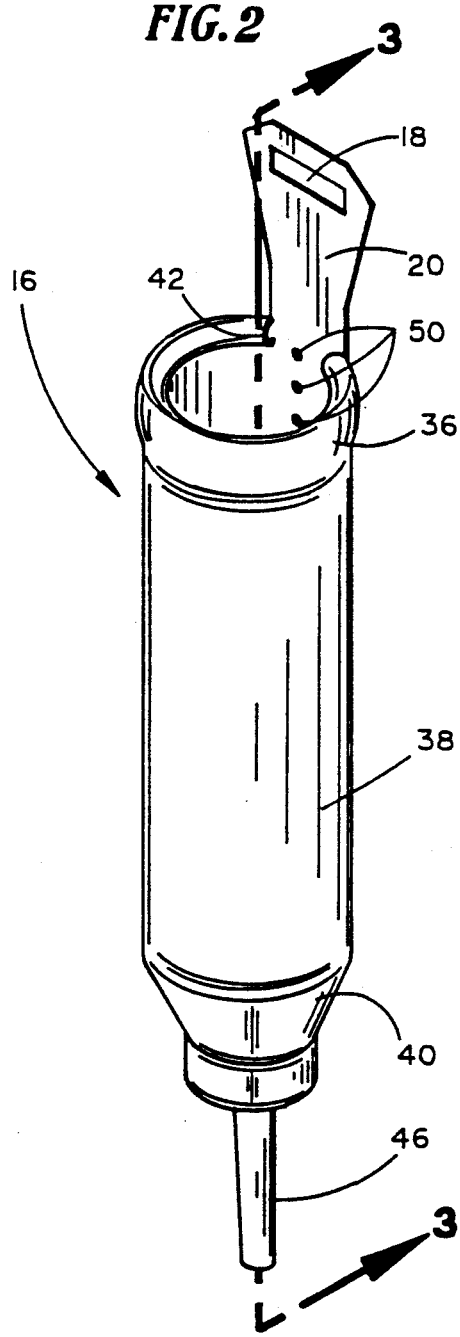
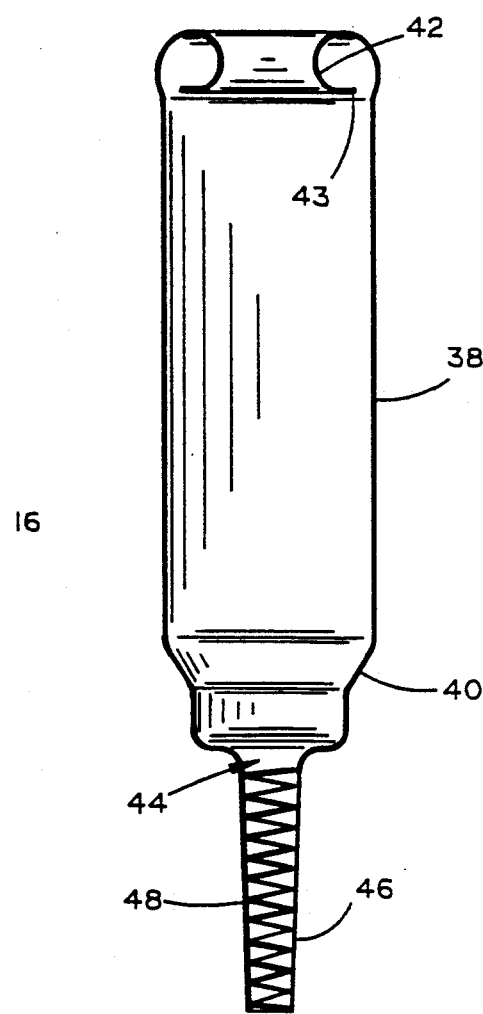
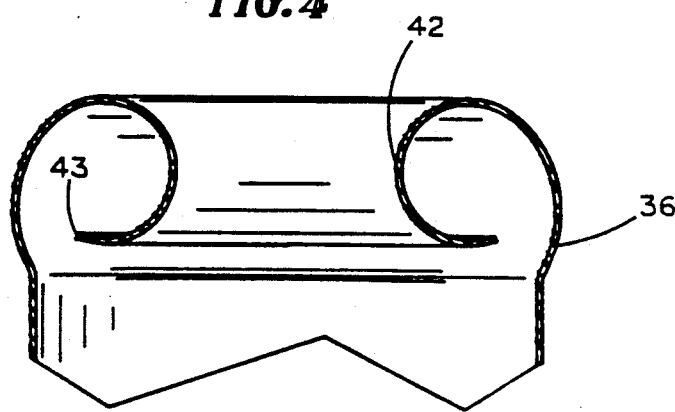

5,084,037

MALE EXTERNAL CATHETER URINE COLLECTION SYSTEM AND SHEATH THEREFOR

BACKGROUND OF THE INVENTION

The invention relates to male external urinary catheters and, more particularly, to an improved sheath for use in a male external catheter urine collection system.

Male incontinence is a not uncommon condition. Its causes are many and diverse, frequently lack of muscular control due to trauma to the subject muscles or nerves.

Many attempts have been made at seeking a satisfactory solution to the problem. Internal catheters are often used with bedridden patients but are generally unsatisfactory for ambulatory men who are otherwise able and wish to lead an active life. A great many external systems have been devised. Each has suffered from one or more deficiencies—an uncomfortable sheath, difficulty in maintaining the sheath in place, closure of a discharge tube due to activities or changes in position of a wearer, leakage around the sheath or in connections between elements of the collection system, and so on.

An object of the present invention, accordingly, is to provide a male external catheter urine collection system and sheath therefor which are easy and comfortable to use and wear, and which remain functional and, substantially leakproof through-out the normal activities of a wearer with an active life-style.

SUMMARY OF THE INVENTION

The invention consists of a male external catheter urine collection system and sheath therefor. The sheath has an open upper end portion, a cylindrical main body portion, and a tapered lower end portion. The sheath is suspended in position by an adjustable belt which includes a depending strap for engaging a tab that extends upwardly from the sheath. The lower end portion of the sheath includes a discharge opening through which the sheath is in communication with a flexible outlet tube. A coil spring associated with the outlet tube acts to prevent closure of the outlet tube by kinking during movement or in certain assumed positions of the wearer. A drainage tube connects to the outlet tube of the sheath and leads to a urine collection bag strapped to the lower leg of the wearer.

BRIEF DESCRIPTION OF THE DRAWINGS

FIG. 2 is an upper perspective view of the sheath of the urine collection system.

FIG. 3 is a cross-sectional view taken along line 3—3 of FIG. 2.

FIG. 4 is an enlarged cross-sectional detail view of the upper end portion of the sheath.

DETAILED DESCRIPTION OF A PREFERRED EMBODIMENT

Figure 1:
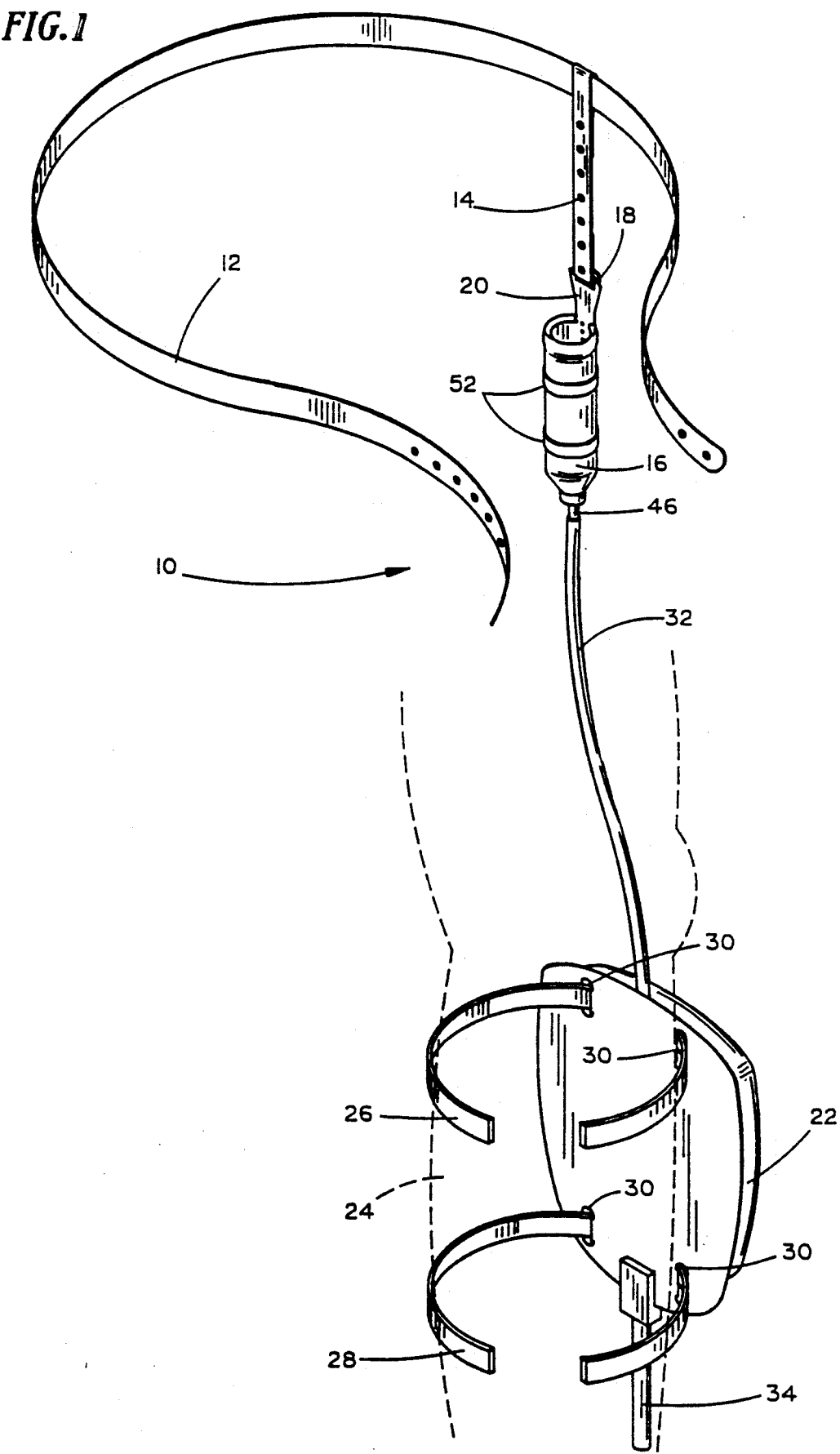
FIG. 1 is a perspective view of the male external catheter urine collection system showing attachment of the urine collection bag to the lower leg of a wearer.

Illustrated in FIG. 1, generally at 10, is a male external catheter urine collection system adapted for wear by an incontinent male to collect and temporarily store urine discharged by the male user of the system 10. The system 10 includes a belt 12 which will encircle the waist of the user and is adjustable in length to adapt to the particular size of the user. A depending vertical strap 14 of adjustable length is attached at its upper end portion to the belt 12 for slidable horizontal adjustment relative thereto. A generally cylindrical sheath 16 includes a vertically extended tab 20 in which is formed a strap-receiving slot 18. The sheath 16 is suspended from the lower end portion of the vertical strap 14 which passes through the slot 18 in the tab 20 to support the sheath 16 at the desired effective and comfortable position.

A urine collection bag 22 is releasably secured to a lower leg 24 of the user by a pair of cushioned straps 26 and 28 which encircle the lower leg 24 and pass through attachment openings 30 in the urine collection bag 22. A discharge tube 32 leads from the sheath 16 down to the urine collection bag 22 to communicate urine present in the sheath 16 to the collection bag 22. A drainage tube 34 is located at the bottom of the urine collection bag 22. A valve (not shown) normally closes the drainage tube 34 to retain collected urine inside the bag 22. If the collection bag 22 is full, however, or if the user desires to empty the bag 22, the valve can be operated to open the drainage tube 34 to empty the bag 22.

The sheath 16 has an open upper end portion 36, a generally cylindrical main body portion 38, and a tapered lower end portion 40. The upper peripheral or terminal edge of the sheath 16 is inwardly overturned, as illustrated at 42 in FIGS. 2–4. The terminal edge 43 is inturned past 180 degrees to a position where it will not grasp or catch the skin of a user upon insertion or withdrawal of the penis of the user from the sheath 16. Moreover, the curved surface of the inwardly overturned edge 42 will be comfortable during use and sufficiently flexible to deform and return to accommodate sundry motions and positions of the user.

The lower end portion 40 of the sheath 16 tapers to a discharge opening at 44 which is in communication with an outlet tube 46 so that any urine present in the sheath 16 will drain downwardly through the discharge opening 44 and into the outlet tube 46. The discharge tube 32 fits over the outlet tube 46 in a tight friction fit that will prevent urine from leaking around the joint.

Associated with the outlet tube 46 is a coil spring 48 (FIG. 3). In the preferred embodiment, the coil spring 48 is held by a friction fit inside the outlet tube 46. Alternatively, the coil spring 48 may be integrally formed with the outlet tube 46 or may be slidably received about the outside of the outlet tube 46. The coil spring 48 functions to prevent the outlet tube 46 from closing due to kinking or excessive bending as may occur during certain motions or in certain positions of the user. The coil spring 48 accommodates the bending of the outlet tube 46 as is necessary to make the urine collection system 10 comfortable but greatly strengthens the outlet tube 46 against radial deformation so that it stays open to allow uninterrupted drainage of urine from the sheath 16 into the discharge tube 32 and hence the collection bag 22 (FIG. 1).

As discussed briefly above, the sheath 16 is designed to be both easy to attach and comfortable to wear. The user's penis is inserted within the open upper end portion 36 of the sheath 16 where the inwardly overturned surface 42 and inturned terminal edge 43 permits unrestricted contact sliding of the sheath 16 over the penis. The sheath 16 is made of a flexible yet sturdy and water tight material. It may be desirable to have the walls of the sheath 16 in the region of the upper end portion 36 thinner than in the main body portion 38 and thus more flexible. Once the user's penis has been inserted within the sheath 16, the belt 12 is attached and adjusted and then the vertical strap 14 is moved to the appropriate horizontal position and adjusted in length to a comfortable position placing the upper end portion 36 of the sheath 16 substantially adjacent the base of the penis. Boxer shorts have been found to increase the comfort of the user by providing a degree of support to the sheath 16 without being unduly restrictive.

The sheath 16 is sized to closely accommodate the penis. If the radial fit is loose, the inturned peripheral edge 42 will be in contact with the outer periphery of the penis but will be deflected toward the outer wall of the sheath 16 only slightly. If the radial fit, however, is tighter, the inturned peripheral edge 42 will flex outwardly to easily accommodate the larger diameter penis. In either event, the inturned terminal edge 42 will act as a partial seal, particularly around the top, underside of the penis where urine tends to collect, especially when the user is seated. The sheath 16 may be manufactured in more than one size to provide additional accommodation to users.

The main body portion 38 of the sheath 16 is of a size to be larger than the penis so that a space exists around the penis between the penis and the main body portion 38. A limited amount of air, therefore, is permitted to circulate inside the sheath 16 and around the penis of the user. This circulation of air is enhanced by three perforations 50 in the top or forward-facing portion of the sheath immediately below the upper peripheral edge thereof. This drying effect enhances the comfort of the system 10 and may decrease the likelihood of dermatitis or other medical complaints associated with skin that is wet for prolonged periods of time. In an alternative embodiment, polytetraflouroethylene (available commercially under the trademark Gore-Tex ®) is incorporated into the sheath 16 to provide a breathable but waterproof membrane to permit enhanced drying without leakage of urine.

To prevent the sheath 16 from being in direct contact with the leg of a user, it may be desirable to wrap the outer periphery of the sheath 16 with two rings of strapping 52 similar to the straps 26 and 28. The strapping rings 52 will cushion the sheath and provide clearance between the leg of a user and the sheath 16.

In normal use, the wearer of the system 10 may at times be seated or have a leg elevated such that the sheath 16 is held in a substantially horizontal position wherein urine may collect somewhat inside the sheath 16. In such cases, the inturned terminal edge 43 will allow the urine to pass into and collect temporarily in the channel formed by the inturned terminal edge 43 and inwardly overturned surface 42. The sheath 16 itself acts as a small volume reservoir that permits the sheath 16 to be in a substantially horizontal or even somewhat upwardly inclined position for limited periods of time the length of which is dependent on the volume of urine flow.

During extended periods of sitting, such as while traveling by car or by airplane, the position of the body may be that urine flow is effectively blocked and collects in the bladder of the incontinent person. In such cases, a large volume of urine may be released over a relatively short period of time when the incontinent person resumes a vertical position. To accommodate such heavy flows, the discharge opening 44 and outlet and discharge tubes 48 and 32 are sufficiently sized to release the flow without overfilling the sheath 16.

The location of the collection bag 22 below the knee of the user further assists in effective operation of the system 10. When the user is seated, the collection bag 22 will still be in a position lower than the sheath 16 so that urine may continue to draw into the collection bag 22. Further, urine will not tend to flow back from the collection bag 22 and into the sheath 16 where it may leak out and wet the user. The system 10 thus functions effectively in a wide variety of positions and motions of a user and permits virtually all normal activities to be performed by the user, including golf, bowling, driving, and jogging, without leakage of urine from the system 10.

In the preferred embodiment, the diameter of the main body section is approximately one and three-quarters inches and the length of the sheath 16 from the top of the tab 20 to the outlet tube 46 is approximately seven and one-half inches. The discharge opening is approximately one-half inch in diameter and the outlet tube has a length of approximately two inches and an inside diameter of approximately one-quarter inch. The inwardly inwardly overturned surface 42 extends approximately one-half inch inwardly from the main body portion 38. The coil spring 48 should be at least approximately one and one-half inches in length.

The above-described preferred embodiments are intended to illustrate the principles of the invention, but not to limit the scope of the invention. Various other embodiments and modifications to these preferred embodiments may be made by those skilled in the art without departing from the scope of the following claims.

What is claimed is:

1. A male external catheter urine collection system, comprising:
   a. sheath having a substantially cylindrical main body portion, an open upper end portion, and a lower end portion having a discharge opening;
   b. an adjustable belt for supporting said sheath;
   c. an outlet tube extended from said lower end portion in communication with said discharge opening;
   d. a coil spring associated with said outlet tube for resisting closure of said outlet tube by kinking, said coil spring, at the same time, allowing for and accommodating at least some bending of said outlet tube thereby making said urine collection system comfortable to a male user;
   e. a collection bag;
   f. conduit means interconnecting said outlet tube and said collection bag for fluid communication between said sheath and said collection bag; and
   g. said open upper end portion includes an inwardly rolled terminal edge which acts to block urine from leakage out of said open edge portion.

2. A urine collection system as defined in claim 1, wherein said collection bag is strapped to a leg of a user below the knee.

3. A urine collection system as defined in claim 1, wherein:
   a. a tab extends upwardly from said open upper end portion for attachment to said belt; and
   b. said open upper end portion includes an inturned terminal edge extended around said open upper end portion from one side of said tab to the other side of said tab, said terminal edge being inturned past 180° in a curved manner.

4. A urine collection system as defined in claim 3, wherein said inturned terminal edge forms a smooth, nonbinding surface for insertion and withdrawal of a penis from said sheath.

5. A sheath for a male external catheter urine collection system, comprising:
 a. a substantially cylindrical main body portion;
 b. an open upper end portion including an inwardly rolled terminal edge which acts to block urine from leakage out of said open upper end portion;
 c. an attachment tab extended upwardly of said open upper end portion for releasable attachment to a support means for the sheath;
 d. a lower end portion having a discharge opening;
 e. an outlet tube connected to said discharge opening; and
 f. a coil spring extended along said outlet tube for resisting closure of said outlet tube by kinking, said coil spring, at the same time, allowing for and accommodating at least some bending of said outlet tube thereby making said urine collection system comfortable to a male user.

6. A sheath as defined in claim 5, further comprising at least one opening near said open upper portion and below said tab for improving air flow inside said sheath.

7. A sheath as defined in claim 5 wherein said inturned terminal edge forms a smooth, nonbinding surface for insertion and withdrawal of a penis form said sheath.

8. A sheath as defined in claim 5, wherein said coil spring is received in a friction fit inside said outlet tube.

9. A sheath as defined in claim 5, wherein said coil spring is integral with said outlet tube.

10. A sheath as defined in claim 5, wherein said terminal edge is inturned past 180° in a curved manner.

* * * * *